United States Patent
Valkenborg et al.

(10) Patent No.: US 11,378,581 B2
(45) Date of Patent: Jul. 5, 2022

(54) MONOISOTOPIC MASS DETERMINATION OF MACROMOLECULES VIA MASS SPECTROMETRY

(71) Applicants: VITO NV, Mol (BE); Universiteit Antwerpen, Antwerp (BE)

(72) Inventors: Dirk Valkenborg, Hasselt (BE); Jef Hooyberghs, Mol (BE); Frank Sobott, Leeds (GB); Kris Laukens, Wilrijk (BE); Frederik Lermyte, Hoevenen (BE)

(73) Assignees: VITO NV, Mol (BE); Universiteit Antwerpen, Antwerp (BE)

( * ) Notice: Subject to any disclaimer, the term of this patent is extended or adjusted under 35 U.S.C. 154(b) by 258 days.

(21) Appl. No.: 16/343,038

(22) PCT Filed: Oct. 20, 2017

(86) PCT No.: PCT/EP2017/076827
§ 371 (c)(1),
(2) Date: Apr. 18, 2019

(87) PCT Pub. No.: WO2018/073404
PCT Pub. Date: Apr. 26, 2018

(65) Prior Publication Data
US 2019/0250168 A1      Aug. 15, 2019

(30) Foreign Application Priority Data

Oct. 20, 2016   (EP) ..................................... 16194868

(51) Int. Cl.
*G01N 33/68* (2006.01)
*G16Z 99/00* (2019.01)
*H01J 49/00* (2006.01)

(52) U.S. Cl.
CPC ......... *G01N 33/6848* (2013.01); *G16Z 99/00* (2019.02); *H01J 49/0036* (2013.01); *G01N 2560/00* (2013.01)

(58) Field of Classification Search
None
See application file for complete search history.

(56) References Cited

U.S. PATENT DOCUMENTS

2007/0114373 A1      5/2007   Zweigenbaum et al.

FOREIGN PATENT DOCUMENTS

| EP | 1 600 776 A2 | 11/2005 |
| EP | 2 590 206 A1 | 5/2013 |

(Continued)

OTHER PUBLICATIONS

Chen Ya-Fen et al: "Determination of accurate protein monoisotopic mass with the most abundant mass measurable using high-resolution mass spectrometry" Analytical Biochemistry, vol. 440, No. I, Jun. 4, 2013 (Jun. 4, 2013). pp. 108-113, XP028676657, ISSN: 0003-2697, DOI: 10.1016/J.AB.2013.05.018 the whole document abstract; figures 1-3 table 2.

(Continued)

*Primary Examiner* — Xiaoyun R Xu
(74) *Attorney, Agent, or Firm* — Banner & Witcoff, Ltd.

(57) ABSTRACT

The present invention provides a method for the determination of the monoisotopic mass of a macromolecule from a mass $M_{mono}$ spectrometry spectrum of said macromolecule based on the experimentally determined most abundant mass, with accuracy in the low parts-per-million (ppm) range. The method uses a simple, double-linear model for predicting the monoisotopic mass based on the experimentally determined most abundant mass, comprising the steps of (a) deriving the most abundant mass MMostAb from the spectrum; and (b) calculating the monoisotopic mass $M_{Mono}$ (Continued)

Figure 1:
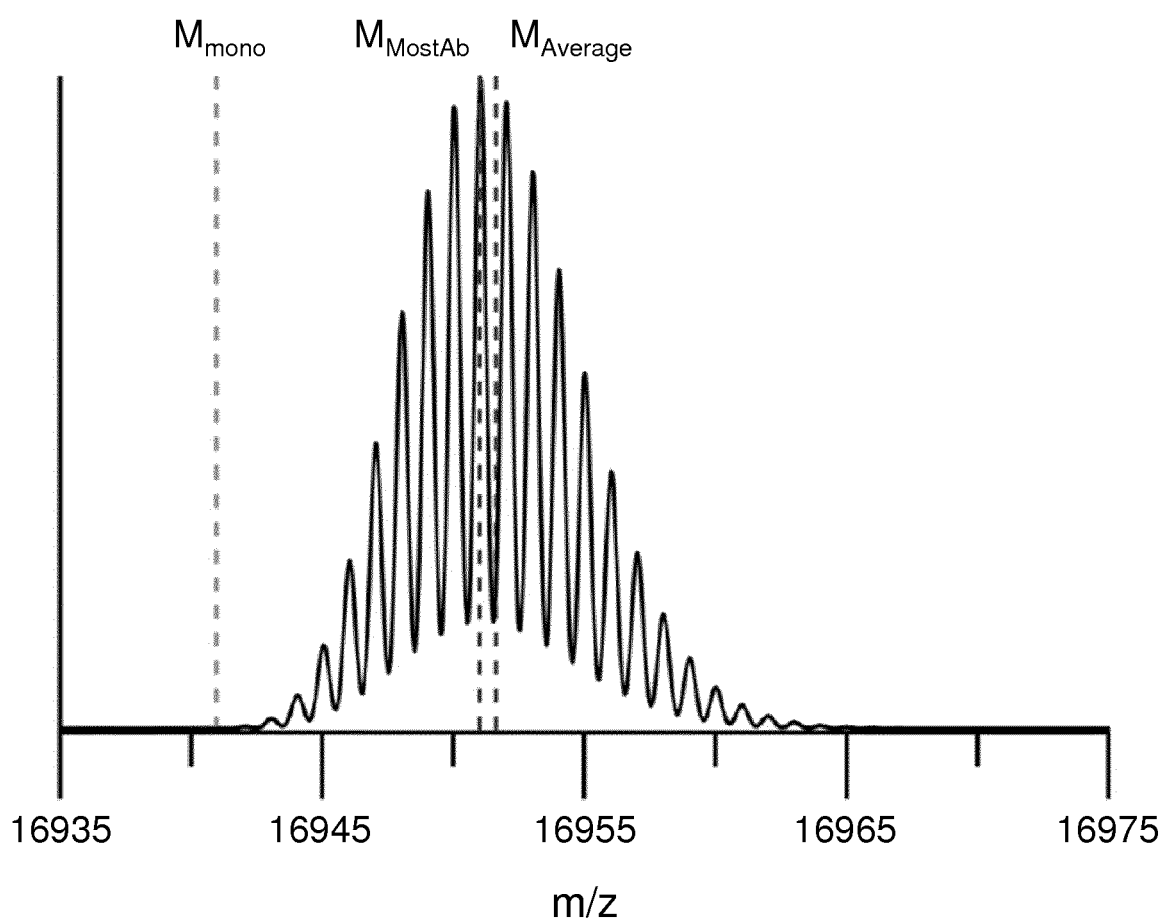

from the most abundant mass $M_{MostAb}$, using $M_{Mono} = a + \beta M_{MOSTAB} + \varepsilon$; wherein $\beta$ is a scalar slope obtainable by fitting the slope of monoisotopic mass versus most abundant mass for a plurality of macromolecules from a macromolecule database; and $\varepsilon$ is a scalar residue of the form $\varepsilon = \varepsilon_{int} + s_{frac}$, $\varepsilon_{int}$ being an integer, and $\varepsilon_{frac}$ being a sawtooth function of $M_{MostAb}$.

12 Claims, 8 Drawing Sheets

(56) References Cited

FOREIGN PATENT DOCUMENTS

| WO | 00/13025 A1 | 3/2000 |
|---|---|---|
| WO | 03/046577 A1 | 6/2003 |
| WO | 03/054772 A1 | 7/2003 |
| WO | 2004/011426 A2 | 2/2004 |
| WO | 2004/025270 A2 | 3/2004 |
| WO | 2004/102180 A2 | 11/2004 |
| WO | 2006/050226 A2 | 5/2006 |
| WO | 2006/106724 A1 | 10/2006 |
| WO | 2014/184320 A1 | 11/2014 |
| WO | 2016/145331 A1 | 9/2016 |

OTHER PUBLICATIONS

Jurgen Claesen et al: "An Efficient Method to Calculate the Aggregated Isotopic Distribution and Exact Center-Masses" Journal of the American Society for Mass Spectrometry, Feb. 1, 2012 (Feb. 1, 2012), XP055021608, ISSN: 1044-0305, DOI: 10.1007/sl3361-0II-0326-2 the whole document.

Senko et al: "Determination of monoisotopic masses and ion populations for large biomolecules from resolved isotopic distributions" Journal of the American Society for Mass Spectrometry, Elsevier Science Inc, US, vol. 6, No. 4, Apr. 1, 1995 (Apr. 1, 1995), pp. 229-233, XP005357128, ISSN: 1044-0305, DOI: 10.1016/1044-0305(95)00017-8 the whole document.

MONOISOTOPIC MASS DETERMINATION OF MACROMOLECULES VIA MASS SPECTROMETRY

RELATED APPLICATIONS

This application is a National Stage Application under 35 U.S.C. 371 of co-pending PCT application PCT/EP2017/076827 designating the United States and filed Oct. 20, 2017; which claims the benefit of EP application number 16194868.2 and filed Oct. 20, 2016 each of which are hereby incorporated by reference in their entireties.

FIELD OF THE INVENTION

The present invention relates to the field of mass spectrometry, in particular to the field of the determination of the mass of a macromolecule, such as a protein particularly in top-down proteomics, and the analysis of isotope distributions.

BACKGROUND TO THE INVENTION

Most elements in the periodic system have variants or isotopes with a different number of neutrons in their nucleus. As elements are defined by their number of protons, these variants possess different masses, but occupy the same place in the periodic system.

The elements occurring in most biomolecules, including the twenty proteinogenic amino acids, i.e. carbon, hydrogen, oxygen, nitrogen, and sulfur, all possess stable isotopes, the most abundant of which is referred to as the monoisotopic variant. The relative amounts of these isotopes are known and relatively constant for terrestrial matter. With the exception of sulfur, which is composed of approximately 94.9% $^{32}S$ and 5.1% heavier isotopes, the other four elements are composed for at least 98.9% of their lightest variant.

As a consequence of the occurrence of multiple isotopes, an ion is visualized by mass spectrometry (MS) as a series of locally correlated peaks, termed the isotope distribution. There is a direct relation between the molecular formula of the ion and the shape of the isotope distribution.

For small molecules, such as metabolites, single amino acids or small peptides, single nucleic acids or small oligonucleotides, the monoisotopic variant (i.e. the variant in which all elements occur in their monoisotopic form) is the most abundant one. While relative abundance of isotopes, and thus the average mass of an element, may vary, monoisotopic masses are a constant of nature, unambiguous and invariant, and therefore an optimal choice for analyte identification and other data processing, e.g. database searching. However, direct measurement of the monoisotopic mass of macromolecules, such as proteins, is in many instances not feasible in practice. Indeed, for intact proteins, made up of thousands of atoms, the probability of encountering the monoisotopic variant actually becomes vanishingly small and this variant will therefore often fall below the limit of detection of contemporary mass spectrometers. Instead, we obtain abundances which follow a somewhat Gaussian-like distribution, as illustrated for apo-myoglobin in FIG. 1.

FIG. 1 illustrates the difference between monoisotopic mass, average mass, and the mass of the most abundant isotope variant (herein also referred to as the "most abundant mass") of equine apo-myoglobin. As can be seen, these three values may be significantly different (up to more than 10 Da). Accordingly, it is not clear, for the purpose of database searching, what is understood to be a protein's mass. In theory, the three aforementioned masses are exactly defined and equally sound, but in practice they have different operational characteristics and behave differently in the presence of noise and uncertainty. With the absence of the monoisotopic variant (i.e. below the detection limit) and the requirement of specialized software to compute the most abundant mass, a weighted average of all observed isotopic variants is often used to measure the observed mass of the proteins. In theory, the average mass of a molecule or protein is conveniently calculated from the average elemental masses and is equally trivial to compute as the monoisotopic mass. An additional argument in favor of using average mass is that this value will be measured if instrument resolution is insufficient to separate isotope peaks, allowing the use of lower-resolution (often less expensive) mass spectrometers.

However, the average mass is quite sensitive to fluctuations in relative isotope abundances, which can occur due to both natural and technical causes [Claesen et al. Anal. Chem. (2015) 87, 10747-10754]. These deviations are often larger than the mass accuracy of modern high-end mass spectrometers and as such, during database identification, a tolerance for deviation of the precursor mass needs to be allowed which is greater than that provided by the instrument capabilities. There is thus a clear impetus for the development of methods for data processing which actually utilize the full instrument capabilities, particularly as these high-end instruments often represent a significant financial investment.

The most abundant mass of an ion is more robust than the average mass toward (limited) natural fluctuations of isotopic abundances [Claesen et al.; Anal. Chem. (2015) 87, 10747-10754] and artefactual perturbations on peak intensities. While the calculation of the most abundant mass is not as trivial as for the average mass, several software packages for simulation of the isotope distribution of macromolecules exist [e.g. as described in Claesen et al.; J Am Soc Mass Spectrom (2012) 23, 753-763; Dittwald et al.; Anal Chem (2013) 85:1991-1994).

Although for large molecules, the most abundant variant is often not visible by mass spectrometry, Dittwald et al (Anal Chem (2013), 85: 1991-1994) discloses a graph wherein $M_{Mono}$ is plotted in function of $(M_{MostAb}-M_{Mono})$ for a selection of more than 50 000 human proteins and a linear relationship between the monoisotopic mass and the mass difference between most abundant peak mass and monoisotopic mass was found. The following linear formula was obtained: $M_{Mono}=0.9994\ M_{MostAb}+0.482$.

The distribution of the residuals from the model predicting the monoisotopic mass from the observed most abundant (peak) mass show a deviation of +/−2 Da, which is too large to be of much practical value. Dittwald et al thus conclude that it is preferable to characterize the mass of large molecules by means of the average mass of an observed isotope cluster.

Using modern high-performance mass spectrometers such as Fourier Transform Ion Cyclotron Resonance (FTICR) or Orbitrap instruments, masses for the (aggregated) isotope peaks can easily be measured with accuracies on the order of only a few ppm, i.e. more accurate than the 2 Da error window shown for the model of Dittwald et al. In addition, due to poor ion statistics, the observed isotope distribution may differ significantly from what is expected based on the elemental composition. For example, tandem MS analysis performed on a liquid chromatography (LC) timescale will typically limit the number of ions in the trap to improve acquisition time. Many other effects exist that can negatively influence ion statistics. This problem is exacerbated in large ions, which exhibit a broad isotope distribution in which several peaks have theoretical intensities only a few percent below that of the most abundant mass. Indeed, at the typical precursor ion populations observed in top-down proteomics, it can be shown that the probability of the experimentally observed most abundant isotope peak not matching the theoretically predicted one, is sufficiently high that it should not be neglected.

Chen et al. [Anal Biochem (2013) 440: 108-113] discloses a method for determining the monoisotopic mass of a protein based on a linear relationship with the most abundant mass, which is a physicochemical property measured with high-resolution mass spectrometry. This method usually produces a number of possible monoisotopic masses, each of a corresponding probability predicted by statistical methods. According to Chen, the mono isotopic mass of a protein is determined from the peak in the mass spectrum which corresponds to the most abundant mass $M_{ma}$, i.e. the most intense signal in an ion cluster. The most abundant mass $M_{ma}$ is identified in the spectrum as such and pre-supposes the use of high end instrumentation with optimal spectral accuracy, which is unaccustomed in the field and much more the exception than the rule. Additionally, as a spectrum is the result of sampling from a larger sample, the accuracy of the mass spectrum and thus the accuracy with which $M_{ma}$ can be determined from the spectrum will depend on the size of the sample. The accuracy with which $M_{ma}$ can be determined from the spectrum will generally be acceptable with molecules with a smaller mass, such as those (insulin, ribonuclease A and other proteins smaller than 60 kDa) on which the method developed by Chen is based.

However, the mass spectrum of macromolecules with a molecular mass substantially above 60 kDa, such as human proteins, will generally contain a large number of correlated peaks with limited intensity variation and reliable determination of $M_{ma}$ from the spectrum will usually not be possible.

Furthermore, recent technological developments allow contemporary mass spectrometrists to generate enormous amounts of data.

Accordingly, there remains at this stage a clear need for the development of suitable methods to assist scientists in distilling useful information from their experimental data, particularly in the analysis of isotope distribution and mass determination.

SUMMARY OF THE INVENTION

The inventors have developed an accurate and robust approach to determine the mass of intact macromolecules with larger masses, in particular biomacromolecules, such as proteins, which alleviate at least some of the problems of the prior art. The inventors have developed a method for the determination of the monoisotopic mass based on the experimentally determined most abundant mass. In particular, the methods of the present invention are based on a simple, double-linear model for predicting the monoisotopic mass based on the experimentally determined most abundant mass, with accuracy in the low parts-per-million (ppm) range. The application of this double-linear model based approach allows for a highly accurate determination of the monoisotopic mass using the most abundant mass, based on the effective relation between monoisotopic and most abundant mass. The methods of the present invention combine the benefits of the most abundant mass (which is robust and easy to detect) with those of the monoisotopic mass (optimal for data processing and molecule identification).

Advantageously, the accurate determination of the mass of the biomacromolecule can be used in the identification of the biomacromolecule. In this context, the methods envisaged herein are particularly useful in top-down proteomics.

The present invention provides a method for determining the monoisotopic mass $M_{Mono} M_{mono}$ of a macromolecule from a mass $M_{mono}$ spectrometry spectrum of said macromolecule, the spectrum comprising a set or plurality of isotopic peaks representing an isotope distribution of said macromolecule, comprising the steps of:

(a) deriving the (experimental) most abundant mass $M_{MostAb}$ from the set or plurality of isotopic peaks; and (b) calculating the monoisotopic mass $M_{Mono}$ from the (experimental) most abundant mass $M_{MostAb}$, using the following model or a mathematical equivalent thereof $M_{Mono} = \alpha + \beta M_{MostAb} + \varepsilon$;

wherein $\beta$ is a scalar slope obtainable by fitting the slope of monoisotopic mass versus most abundant mass for a plurality of macromolecules from a macromolecule database; $\alpha$ is the intercept, and $\varepsilon$ is a scalar residue of the form $\varepsilon = \varepsilon_{int} + \varepsilon_{frac}$, $\varepsilon_{int}$ being an integer, and $\varepsilon_{frac}$ being a sawtooth function of $M_{MostAb}$.

The method of this invention makes use of the linear relationship observed between a set of known most abundant masses and a set of monoisotopic masses for a plurality of known macromolecules from a macromolecular database, to determine the monoisotopic mass of an unknown macromolecule.

In particular embodiments of the present invention, the macromolecule is a protein.

In particular embodiments of the present invention, the domain of $\varepsilon_{frac}$ is [0,1], more in particular $\varepsilon_{frac} = \varepsilon - \text{round}(\varepsilon)$, with round($\varepsilon$) being the round function of $\varepsilon$.

In particular embodiments of the present invention, $\varepsilon_{int}$ is an integer selected from the list consisting of −2, −1, 0, 1, and 2, preferably wherein $\varepsilon_{int}$ is selected from the list consisting of −1, 0, and 1. In particular embodiments of the present invention, selecting $\varepsilon_{int}$ comprises the steps: modelling or quantifying the probability of $\varepsilon_{int}$ being −1, 0, or 1 as a function of the most abundant mass $M_{MostAb}$; and selecting −1, 0, or 1 as the value of $\varepsilon_{int}$ when the probability or quantity that $\varepsilon_{int}$ equals −1, 0, or 1, respectively, is the highest.

In particular embodiments of the present invention, $\beta$ ranges between 0.99 and 1.

In particular embodiments of the present invention, step (a) comprises the steps of:

(a1): calculation of the average mass $M_{Average}$ (exp) of the plurality of isotopic peaks within the mass spectrum of the macromolecule and selection of the experimental most abundant mass $M_{MostAb}$ (exp) as the isotopic peak with the highest intensity in the plurality of isotopic peaks within the mass spectrum.

(a2): calculation of $[M_{Average} (\exp) - M_{MostAb} (\exp)]$ in order to determine if $M_{MostAb}$ (exp) corresponds to the theoretical $M_{MostAb}$;

(a3). if $0.1 \leq [M_{Average} (\exp) - M_{MostAb} (\exp)] \leq 1.1$, then MostAb (exp) is selected as the correct $M_{MostAb}$, corresponding to the theoretical most abundant mass.

if not $0.1 \leq [M_{Average} (\exp) - M_{MostAb} (\exp)] \leq 1.1$; then the correct $M_{MostAb}$ (exp, cor) is selected as the mass corresponding to the mass of the peak positioned one or two peaks before or after the $M_{MostAb}$ (exp) isotopic peak so that $0.1 \leq [M_{Average} (\exp) - \{M_{MostAb} (\exp, \text{cor})\}] \leq 1.1$, wherein $M_{MostAb}$ (exp,cor) is selected as the correct $M_{MostAb}$, corresponding to the theoretical most abundant mass.

This step permits verifying whether $M_{MostAb}$ that has been identified from the mass spectrum, effectively corresponds to the theoretical $M_{MostAb}$ for a certain macromolecule. The method of this invention is therefore not only suitable for identifying $M_{MostAb}$ for small molecules with a mass up to 60 kDa, but also for macromolecules with substantially larger masses.

In other particular embodiments of the present invention, in step (a), the most abundant mass $M_{MostAb}$ is approximated by the most abundant mass of a scaled averagine model, the scaled averagine model having an average mass equal to the average mass of the isotopic mass spectrum of the macromolecule, in particular a protein or polypeptide.

In particular embodiments of the present invention, the method is a computer-implemented method.

In particular embodiments of the present invention, the method further comprises the step (c) of identification of the macromolecule using $M_{Mono}$ of step (b).

The present invention further provides a computer program product comprising computer-readable instructions which, when executed on a computer, cause the computer to execute a method according to the present invention as detailed herein.

FIGURE LEGENDS

The following description of the figures of specific embodiments of the methods and instruments described herein is merely exemplary in nature and is not intended to limit the present teachings, their application or uses.

FIG. 1 represents a simulated isotope distribution of equine apo-myoglobin (Uniprot entry P68082; chemical formula $C_{769}H_{1212}N_{210}O_{218}S_2$, average mass 16951.26 Da), at a resolution of 30000 (FWHM). Differences between the monoisotopic, most abundant, and average masses are expressed both in absolute values, as well as fractions of the most abundant mass (expressed in ppm).

Figure 2A:
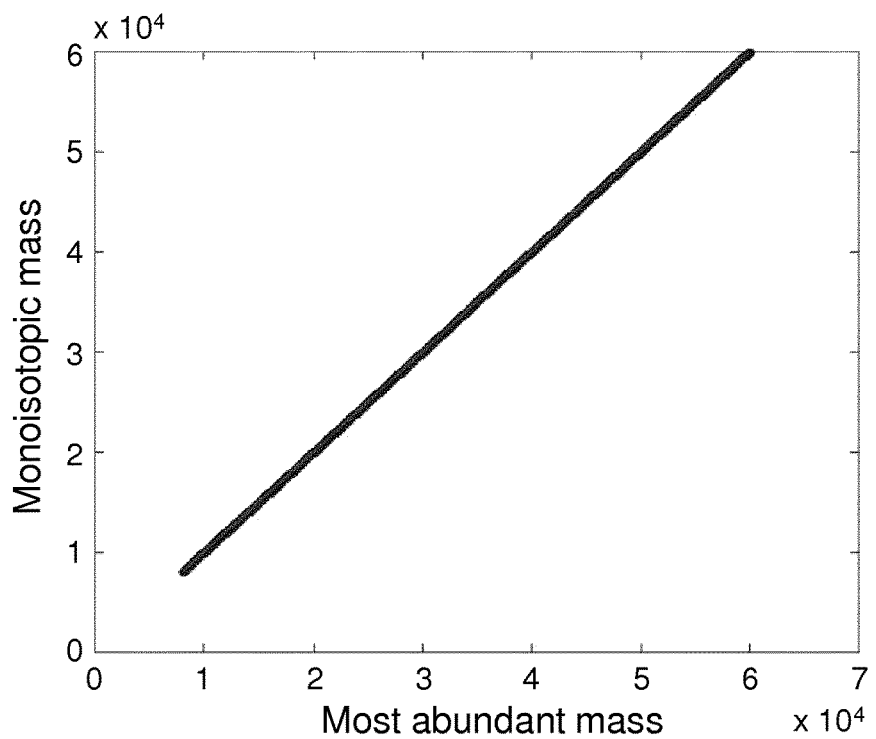
Figure 2B:
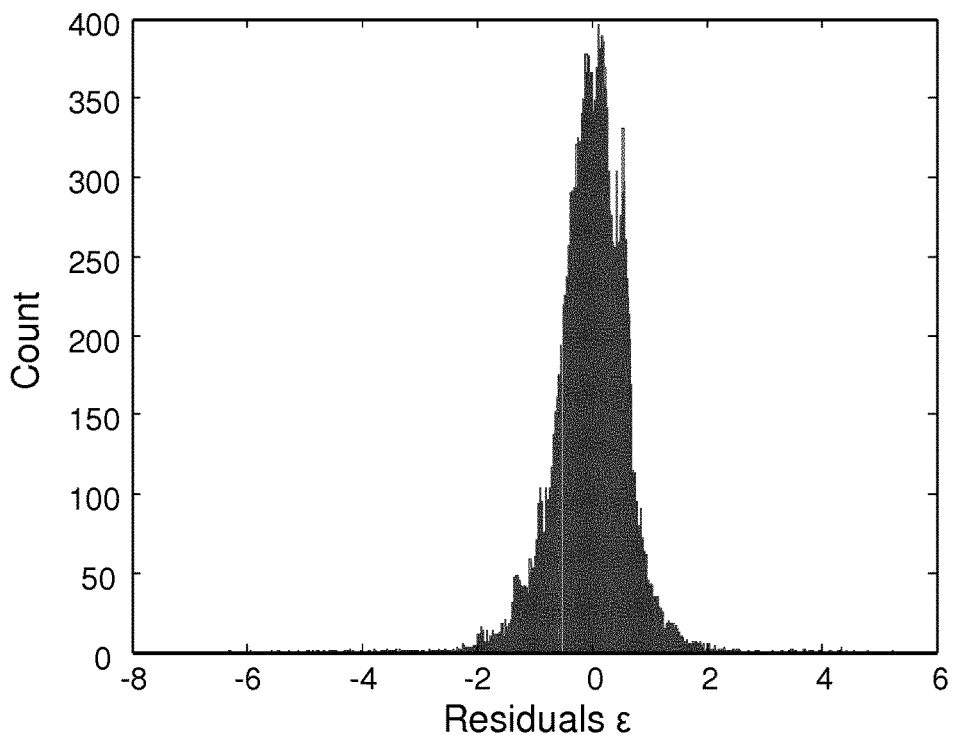
Figure 2C:
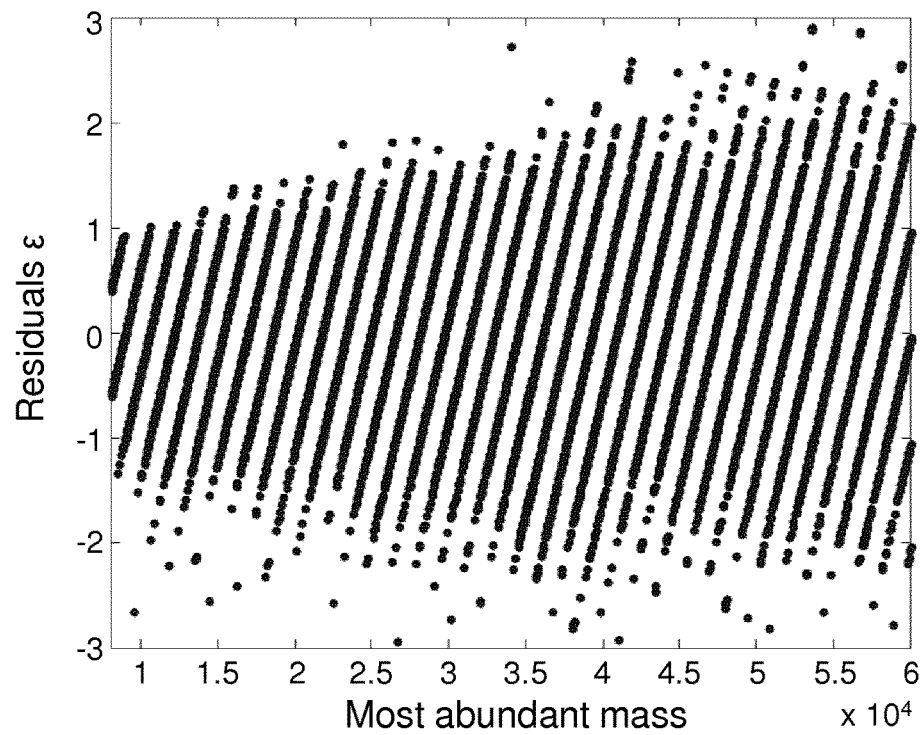

FIG. 2A shows the approximately linear correlation observed between the monoisotopic mass $M_{Mono}$ and most abundant mass $M_{MostAb}$ of human proteins in the UniProt database. FIG. 2B represent a histogram of values of the residues ε, showing the residues are nearly always found between −2 and +2. FIG. 2C presents a plot of ε versus $M_{MostAb}$, revealing a structure in the deviation from this simple linear model, with the fractional part of ε ($ε_{frac}$) shown in FIG. 2D. FIG. 2E shows the percentage of samples having residuals near 0, −1 or +1 in function of $M_{MostAb}$, indicating the periodicity in the nearest integer value to ε, allowing prediction of the integer part of ε ($ε_{int}$).

Figure 3:
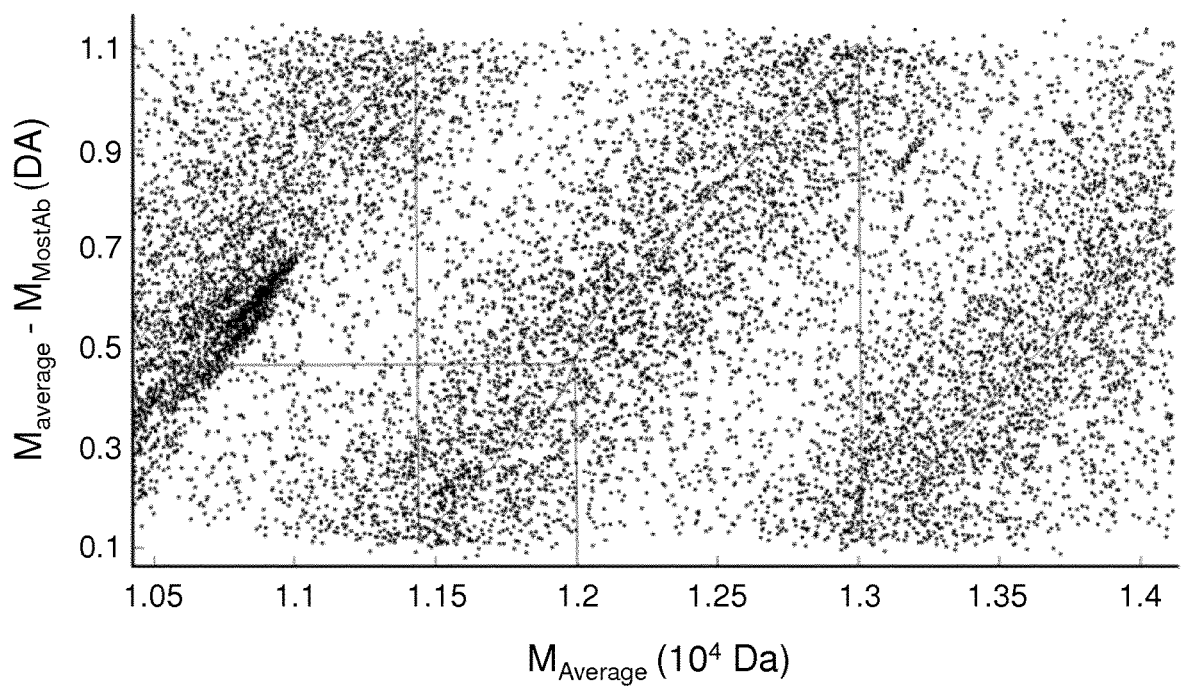

FIG. 3 shows a plot of the values of ($M_{Average} - M_{MostAb}$) vs. $M_{Average}$ for human proteins in the UniProt database, showing this difference almost always has a value between 0 and 1, and revealing periodicity as a function of $M_{MostAb}$.

FIG. 4 represents histograms summarizing the results from 200 spectra of equine apo-myoglobin. (A) Observed values of the most intense isotope peak; (B) observed values of ($M_{Average} - M_{MostAb}$); (C) corrected values of the most intense isotope peak; (D) the deviation of the calculated average mass (obtained from the spectra) from the theoretical average mass, expressed in ppm; (E) deviation of the calculated monoisotopic mass (determined using the methods of the present invention) from the theoretica monoisotopic value for the 200 spectra, expressed in ppm.

Figure 5:
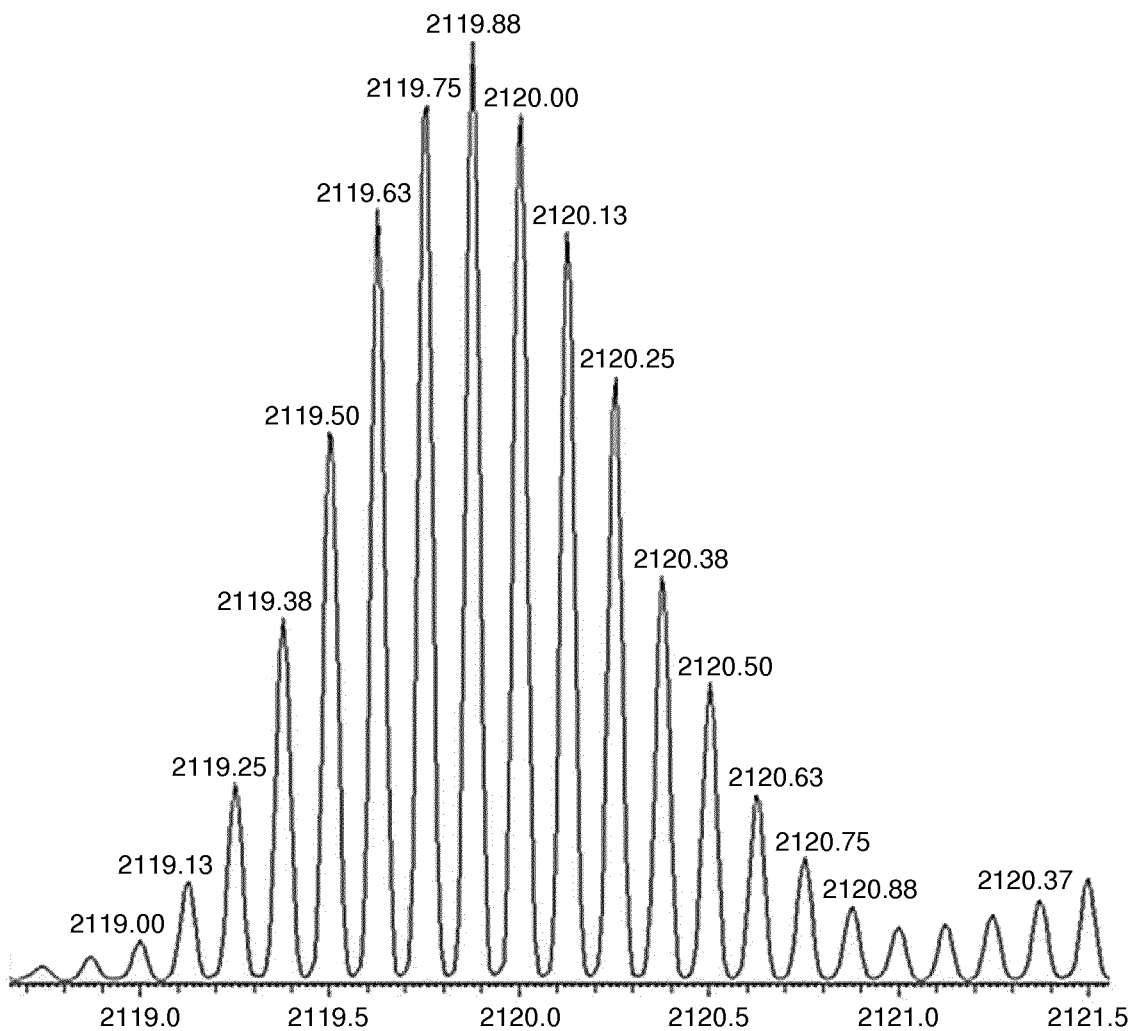

FIG. 5 schematically represents a particular embodiment of the method of the present invention.

DETAILED DESCRIPTION OF INVENTION

Before the present system and method of the invention are described, it is to be understood that this invention is not limited to particular systems and methods or combinations described, since such systems and methods and combinations may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

The term "monoisotopic mass" or $M_{mono}$ means the sum of the masses of the atoms in a molecule using the mass of the principal (most abundant) isotope for each element instead of the isotopic average mass. For typical organic compounds, like proteins, polynucleotides or polysaccharides, the monoisotopic mass results in the lightest isotope being selected. Monoisotopic mass is typically expressed in Daltons (Da) or unified atomic mass units (u).

The term "average mass" or $M_{Average}$ corresponds to the sum of the masses of the atoms in a molecule using the isotopic average mass for each element. The "experimentally determined average mass" or "experimental average mass" refers to the average mass calculated as a weighted sum of the observed masses and intensities of the isotopic peaks from the mass spectrum of a molecule.

The term "most abundant mass" or $M_{MostAb}$ corresponds to the mass of the isotope variant with the highest probability of occurrence. For a given macromolecule, specifically but not limited to a protein or polypeptide, this mass may be calculated via software packages that simulate the isotopic distribution of macromolecules (proteins) for mass spectrometry. For a given set of isotopic peaks within a mass spectrum of a molecule, the most abundant mass is the mass of the most abundant isotope variant, i.e. the isotopic peak with the highest intensity of the set of isotopic peaks within a mass spectrum of a molecule.

The term "accuracy" or "mass accuracy" as used herein relates to the difference between the expected or theoretical mass $m_e$ (in Dalton) and the observed or experimentally determined mass $m_o$ (in Dalton) according to the formula:

$$\text{accuracy} = \frac{|m_o - m_e|}{m_e} \times 10^6$$

Accuracy is expressed in ppm. In this context, the mass accuracy of Orbitrap class MS instruments is about 2 ppm.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

In the present description of the invention, reference is made to the accompanying drawings that form a part hereof, and in which are shown by way of illustration only of specific embodiments in which the invention may be practiced. It is to be understood that other embodiments may be utilised and structural or logical changes may be made without departing from the scope of the present invention. The following detailed description, therefore, is not to be taken in a limiting sense, and the scope of the present invention is defined by the appended claims.

The inventors have developed a simple double-linear model which predicts or which permits to identify the monoisotopic mass $M_{Mono}M_{mono}$ of a macromolecule based on the most abundant mass $M_{MostAb}$ from a series of isotopic peaks within a MS spectrum, with an accuracy in the low ppm range, or stated differently, with an accuracy of the same order of magnitude as the accuracy of current high-performance mass spectrometers. Determining the monoisotopic mass $M_{Mono}M_{mono}$ of a macromolecule with high accuracy is primordial to permit a reliable identification of the macromolecule.

Thus, in a first aspect the present invention provides a method for determining the monoisotopic mass $M_{Mono}$ $M_{mono}$ of a macromolecule from a mass $M_{mono}$ spectrometry spectrum of said macromolecule, the spectrum comprising a set or plurality of isotopic peaks representing an isotope distribution of said macromolecule, comprising the steps of:
(a) deriving the most abundant mass $M_{MostAb}$ from the set or plurality of isotopic peaks within the mass spectrum; and
(b) calculating the monoisotopic mass $M_{Mono}$ from the most abundant mass $M_{MostAb}$, using the model or a mathematical equivalent thereof according to the equation 1:

$$M_{Mono} = \alpha + \beta M_{MostAb} + \varepsilon; \tag{Eq. 1}$$

wherein $\beta$ is a scalar slope obtainable by fitting the slope of the plot of monoisotopic mass $M_{Mono}$ in function of the most abundant mass $M_{MostAb}$ for a plurality of macromolecules from a macromolecule database; $\alpha$ is the intersect, and $\varepsilon$ is a scalar residue of the form $\varepsilon = \varepsilon_{int} + \varepsilon_{frac}$, $\varepsilon_{int}$ being an integer, and $\varepsilon_{frac}$ being a sawtooth function of $M_{MostAb}$.

Preferably, the method as envisaged herein is a computer-implemented method.

The present invention thus relates to improved methods for the analysis or interpretation of spectra obtained by mass spectrometry, in particular of spectra of macromolecules comprising a plurality of isotopic peaks, i.e. a series of regularly spaced peaks representing the isotopic distribution of the macromolecule.

The invention as envisaged herein is particularly suitable for the determination of $M_{Mono}$ for macromolecules, i.e. molecules of high molecular mass having a structure which essentially comprises of the multiple repetition of units derived from molecules (or subunits) of low molecular mass. In particular embodiments said macromolecule is a biomacromolecule. In particular embodiments, said biomacromolecule is a protein or polypeptide (made up of amino acids), a polynucleotide (DNA or RNA) (made up of nucleic acids) or a polysaccharide (made up of monosaccharides). In the context of the present invention, the term "poly" as in polypeptide, polynucleotide or polysaccharide corresponds to at least 10 subunits. Thus a polypeptide, polynucleotide or polysaccharide comprises at least 10 amino acid residues, at least 10 nucleic acid residues, or at least 10 monosaccharides, respectively. In particularly preferred embodiments, the present invention is particularly suited for the determination of $M_{Mono}$ of a protein and the subsequent identification and/or quantification of proteins, such as in top-down proteomics.

The term "macromolecule" within the scope of this invention generally refers to molecules, in particular biomolecules, for example proteins but not limited thereto, with a mass substantially above 60 kDa, for example at least $10^5$ Da, at least at least $10^6$ Da, at least $10^8$ Da, or at least $10^9$ Da. Although the method of this invention is particularly suitable for the identification of macromolecules with high molecular mass, it is also suitable for the identification of macromolecules with smaller molecular masses, for example a molecular mass of at least $10^3$ Da, preferably at least $10^4$ Da, more preferably at least $10^5$ Da.

The skilled person understands that the methods as envisaged herein are not limited to particular mass spectrometers, and does as such not presuppose the use of high end, high resolution mass spectrometers. However, the invention is particularly suitable for analysing a mass spectrum obtained on high-performance mass spectrometers such as Fourier Transform Ion Cyclotron Resonance (FTICR) or Orbitrap instruments, having accuracies in the order of only a few ppm. Advantageously, the present invention allows determination of $M_{Mono}$ within a few ppm, in line with the accuracy and precision of these high performance instruments.

In the methods as envisaged herein, the model or a mathematical equivalent thereof according to the equation 1 used in step (b) is obtainable by fitting the slope of the plot of monoisotopic mass $M_{Mono}$ in function of the most abundant mass $M_{MostAb}$ for a plurality of macromolecules, such as macromolecules from a macromolecule database.

More in particular, for obtaining the model according to equation 1, firstly, theoretical values for $M_{Mono}$ and $M_{MostAb}$ are derived for a plurality of macromolecules, such as from a macromolecule database, e.g. a protein database. As indicated above, $M_{Mono}$ of each macromolecule in the database corresponds to the sum of the masses of the atoms in the macromolecule using the mass of the principal (most abundant) isotope for each element instead of the isotopic average mass. For each macromolecule in the database, $M_{MostAb}$ is typically derived from a simulated isotope distribution using suitable algorithms or software, such as e.g. BRAIN algorithm (Claesen et al.; J Am Soc Mass Spectrom (2012) 23: 753-763; Dittwald P et al.; Anal Chem (2013), 85(4): 1991-1994; both incorporated herein by reference).

Next, the monoisotopic mass $M_{Mono}$ of each entry within the database is plotted against the most abundant mass $M_{MostAb}$ and an approximately linear relation with slope $\beta$ and intercept $\alpha$ is obtained.

The linear relation can be described by equation 1; i.e. $M_{Mono}=\alpha+\beta M_{MostAb}+\varepsilon$; (Eq. 1), wherein $M_{Mono}$ is the monoisotopic mass, and $M_{MostAb}$ is the most abundant mass, wherein $\beta$ is a scalar slope obtainable by fitting the slope of monoisotopic mass $M_{Mono}$ versus most abundant mass $M_{MostAb}$ for a plurality of macromolecules from a macromolecule database; $\alpha$ is the intersect, and $\varepsilon$ is a scalar residue.

The actual deviations between this model and the actual monoisotopic masses are represented by the residuals, $\varepsilon$.

Next, the residuals $\varepsilon$ are plotted in function of $M_{MostAb}$, showing that the different values are found on a set of parallel trend lines. This means that a given particular value of the most abundant mass $M_{MostAb}$ corresponds to several values for the residual $\varepsilon$, intersecting with multiple different trend lines. Each intersect or value for the residual $\varepsilon$ indicates a possible solution for the monoisotopic mass for that particular value of the most abundant mass $M_{MostAb}$. The possible solutions differ from each other with an integer mass difference. Thus, the residuals have a direct relation with the most abundant mass, apart from the integer mass difference ($\Delta i$) between the monoisotopic and most abundant peak.

Therefore, each value of $\varepsilon$ can be decomposed into an integer part $\varepsilon_{int}$ and a fractional part $\varepsilon_{frac}$, wherein $\varepsilon_{frac}$ is computed according to equation 2:

$$\text{frac}(\varepsilon)=\varepsilon_{frac}=\varepsilon-\text{round}(\varepsilon) \quad \text{(Eq. 2)}$$

wherein round($\varepsilon$) denotes the round function of $\varepsilon$. As such, $\varepsilon_{frac}$ is always positive. Moreover, only a single value for $\varepsilon_{frac}$ corresponds to a given particular $M_{MostAb}$, as can be seen when $\varepsilon_{frac}$ is plotted as a function of $M_{MostAb}$, neglecting the integer part ($\varepsilon_{int}$). The result is a sawtooth pattern which can be easily modelled, resulting in a specific linear relation for a given $M_{MostAb}$.range. The vast majority of $\varepsilon_{int}$ values are at 0 or ±1 Da, with only 3.8% at ±2 Da, and the values ±3 or ±4 Da together occurring in less than 0.05% of cases. As such, for over 96% of all proteins, the modelled saw tooth pattern, such as e.g. shown in FIG. 2D, allows, for a given value of $M_{MostAb}$, to calculate three potential values for $M_{Mono}$, spaced 1 Da apart, one of which is very likely to match the theoretical value to within a few ppm.

A final refinement of the model allows to model the probability of the variants of monoisotopic masses with different values of $\varepsilon_{int}$. This may be performed by plotting the probability to the nearest integer value to the residuals as a function of $M_{MostAb}$, allowing to arrive at a single predicted $M_{MostAb}$ value.

In particular embodiments of the present invention, the parameter $\beta$ in the linear model represented by Equation 1 is about 1, in particular $\beta$ ranges between 0.9 and 1, more in particular $\beta$ ranges between 0.99 and 1; even more in particular $\beta$ ranges between 0.999 and 1.

In certain embodiments of the method envisaged herein, the domain of $\varepsilon_{frac}$ is [0,1], more particularly, in certain embodiments of the methods as envisaged herein, $\varepsilon_{frac}=\varepsilon-$round($\varepsilon$), with round($\varepsilon$) being the round function of $\varepsilon$.

In particular embodiments of the present invention, the slope of each linear part of the sawtooth model, obtained when $\varepsilon_{frac}$ is plotted as a function of $M_{MostAb}$ and neglecting the integer part ($\varepsilon_{int}$), ranges between $6.2\times10^{-4}$ and $6.3\times10^{-4}$, preferably ranges between $6.24\times10^{-4}$ and $6.27\times10^{-4}$. In particular embodiments of the present invention, the period of the sawtooth function ranges between 1550 and 1650 Dalton, more particularly ranges between 1575 and 1625 Dalton.

In certain embodiments of the methods as envisaged herein, $\varepsilon_{int}$ is an integer selected from the list consisting of −2, −1, 0, 1, and 2, preferably wherein $\varepsilon_{int}$ is selected from the list consisting of −1, 0, and 1. In more particular embodiments, selecting $\varepsilon_{int}$ comprises the steps of (i) modelling the probability of $\varepsilon_{int}$ being −1, 0, or 1 as a function of the most abundant mass $M_{MostAb}$; and selecting −1, 0, or 1 as the value of $\varepsilon_{int}$ when the probability that $\varepsilon_{int}$ respectively equals −1, 0, or 1 is the highest. Alternatively, the amount of error (−1, 0 or +1) can be quantified after predicting the monoisotopic mass and presented in table format.

The skilled person understands that these steps can easily be followed to generate a model for different classes of macromolecules, in particular proteins, for different organisms (plants or animals, e.g. mammals), or even species, if necessary. In preferred embodiments of the methods envisaged herein, particularly computer implemented methods as envisaged herein, the model is developed only once for a certain class of biomolecules, organisms (plants, animals), organisms (mammals) and/or species (homo sp.), and the model parameters are subsequently stored in a computer memory for further use. Advantageously, the determination of a monoisotopic mass for a particular most abundant mass, derived from a series of isotopic peaks within a MS spectrum, has a low computational cost as only two linear models need to be evaluated, with the first linear model corresponding to equation 1, and the second linear model corresponding to the sawtooth function, wherein the relevant part of the sawtooth function is determined by the observed or calculated most abundant mass $M_{MostAb}$.

In particular embodiments, the methods of the present invention further include the initial steps of obtaining a mass spectrum of a biomacromolecule, such as a protein or polypeptide, and determining the experimentally most abundant mass after isotopic peak picking and charge deconvolution, as well understood to the skilled person.

In certain embodiments of the methods envisaged herein, step (a) comprises selecting the mass corresponding to the peak with the highest intensity as $M_{MostAb}$. However, certain factors, noise etc, can cause a minor distortion of the relative intensities of isotope peaks, so that the experimentally observed $M_{MostAb}$ does not correspond to the theoretically derived $M_{MostAb}$ based on the simulation of the isotope distribution for a macromolecule.

Accordingly, in preferred embodiments certain steps may be taken to select the correct $M_{MostAb}$ in step (a).

In preferred embodiments of the methods envisaged herein, step (a) comprises the steps of:

(a1): calculation of the average mass $M_{Average}$ (exp) of the plurality of isotopic peaks within the mass spectrum of the macromolecule, or within a sum spectra of multiple recorded mass spectra of the macromolecule, and selection of the most abundant mass $M_{MostAb}$ (exp) as the isotopic peak with the highest intensity in the plurality of isotopic peaks.

(a2): calculation of $[M_{Average}$ (exp)$-M_{MostAb}$ (exp)$]$, particularly for each of the multiple spectra and plotting $[M_{Average}$ (exp)$-M_{MostAb}$ (exp)$]$ of each of the multiple spectra in a histogram, in order to determine if $M_{MostAb}$ (exp) corresponds to the theoretical $M_{MostAb}$;

(a3). if $0.1 \leq [M_{Average}$ (exp)$-M_{MostAb}$ (exp)$] \leq 1.1$, then $M_{MostAb}$ (exp) is selected as the correct $M_{MostAb}$, corresponding to the theoretical most abundant mass.

if not $0.1 \leq [M_{Average}$ (exp)$-M_{MostAb}$ (exp)$] \leq 1.1$; then the correct $M_{MostAb}$ (exp, cor) is selected as the mass corresponding to the mass of the peak positioned one or two peaks before or after the $M_{MostAb}$ (exp) isotopic peak so that $0.1 \leq [M_{Average}$ (exp)$-\{M_{MostAb}$ (exp, cor)$\}] \leq 1.1$, wherein $M_{MostAb}$ (exp,cor) is selected as the correct $M_{MostAb}$, corresponding to the theoretical most abundant mass.

In other preferred embodiments, step (a) comprises the step of approximating the most abundant mass $M_{MostAb}$ as the most abundant mass of a scaled averagine model, as described in Senko et al. (J Am Soc Mass Spectrom (1995) 6: 229-233), which is herein incorporated by reference, wherein the scaled averagine model has an average mass equal to the average mass of the isotopic MS spectrum of the protein.

In other embodiments, step (a) comprises increasing the number of charges.

Advantageously, the accurate determination of $M_{Mono}$ contributes to a more accurate identification of the macromolecule, particularly the more accurate identification of a protein, such as in top-down proteomics.

Accordingly, preferred embodiments of the methods envisaged herein further comprise the step: (c) identification of the macromolecule using $M_{Mono}$ of step (b). In certain embodiments, step (c) includes searching a database of biomacromolecules, such as a protein database, using the $M_{Mono}$ and selecting the one or more biomacromolecules with matching monoisotopic mass.

Referring to FIG. 5, a particularly preferred embodiment of the method of the present invention is schematically represented as a work flow to derive the monoisotopic mass from a given mass spectrum of an unknown biomacromolecule, such as a protein. Isotopic peak picking and charge deconvolution allows to derive the (experimental) most abundant mass from the mass spectrum of the unknown biomacromolecule. This value is introduced in both the first linear model, represented by equation 1, as in the sawtooth function, and for assessing the probabilities of $\varepsilon_{int}$ being $-1$, 0, or 1. The combination of these mathematical operations results in the (theoretical) monoisotopic mass for the unknown spectrum. Optionally, this monoisotopic value can then be cross referenced with a relevant database for identifying the unknown biomacromolecule.

Another aspect of the present invention provides a computer program product comprising computer-readable instructions which, when executed on a computer, cause the computer to execute a method as envisaged herein.

The present invention is further illustrated in the following examples.

EXAMPLES

Example 1—Development of the Model Representing the Relation Between Monoisotopic Mass & Most Abundant Mass The model (and algorithm) described herein was developed using 98616 human proteins (78328 after removing redundant sequences) with a mass between 8-60 kDa in the UniProt database. Although this model and the below cited model parameters may be valid for mammalian proteins as well, the skilled person understands that a similar workflow can easily be followed to generate a model for different classes of proteins, or biomacromolecules in general, if necessary.

The BRAIN algorithm (Claesen et al.; J Am Soc Mass Spectrom (2012) 23: 753-763; Dittwald P et al.; Anal Chem (2013), 85(4):1991-1994; both incorporated herein by reference) was used to model the isotope distribution of each protein, and to obtain the most abundant mass for each sequence. The monoisotopic and average mass for each sequence was obtained based on the mass of the principal (most abundant) isotope for each element and the isotopic average mass, respectively.

Next, the monoisotopic mass vs. most abundant mass for each entry within the database was plotted and an approximately linear relation with intersect ($\alpha$, in the present case $\alpha=0{,}607447104$) and slope ($\beta$) just below unity is observed (i.e. in the present case $\beta=0{,}999372854$), as can be intuitively expected (FIG. 2A). This is described by the following equation:

$$M_{Mono} = \alpha + \beta \cdot M_{MostAb} + \varepsilon$$

wherein $M_{Mono}$ is the monoisotopic mass, and $M_{MostAb}$ is the most abundant mass.

The deviations between this model and the actual monoisotopic masses are represented by the residuals, $\varepsilon$. For approximately 65% of all proteins, $|\varepsilon| \leq 0.5$ Da, and for 99% of proteins, $|\varepsilon| \leq 2$ Da (FIG. 2B). However, as indicated before, these deviations are too large for this simple linear model to be of much practical value.

Next, the residuals $\varepsilon$ were plotted in function of $M_{MostAb}$, as shown in FIG. 2C. The plot shows that the different values are found on a set of trend lines. When representing a given particular most abundant mass $M_{MostAb}$ by a vertical line, this line will intersect a few of these trend lines. Each intersect indicates a possible solution for the monoisotopic mass given the most abundant mass. Interestingly, the possible solutions exhibit an unexpected relation between each other as they differ with an integer mass difference. Thus, the residuals have a direct relation with the most abundant mass, apart from the integer mass difference (Δi).

The residuals $\varepsilon$ therefore contain structure and relevant information and are not randomly scattered on the $[-2; +2]$ Da range, but appear in distinct groupings. The two or three possible values of $M_{Mono}$ (corresponding to as many possible values of $\varepsilon$) predicted for each value of $M_{MostAb}$ are thus due to different integer values for Δi. These result from differences in the atomic composition that influence the shape of the isotope distributions of the proteins found on different trend lines in the same mass range, e.g., as a result of different amounts of sulfur-containing residues. As such, these possible values are spaced 1 Da apart. Therefore, each value of ε can be decomposed into an integer part $\varepsilon_{int}$ and a fractional part $\varepsilon_{frac}$, wherein $\varepsilon_{frac}$ is computed according to the formula:

$$\mathrm{frac}(\varepsilon) = \varepsilon_{frac} = \varepsilon - \mathrm{round}(\varepsilon)$$

Wherein round(ε) denotes the round function. As such, $\varepsilon_{frac}$ is always positive, for example, frac(1.2)=1.2−round(1.2)=1.2−1=0.2 and frac(−0.8)=−0.8−round(−0.8)=−0.8−(−1)=0.2. Even though this model is still too simple to allow unambiguous prediction of monoisotopic mass, we see that the consistent spacing between potential values for $\varepsilon_{frac}$ is equivalent to having only a single value for $\varepsilon_{frac}$ corresponding to a given $M_{MostAb}$.

Figure 2D:
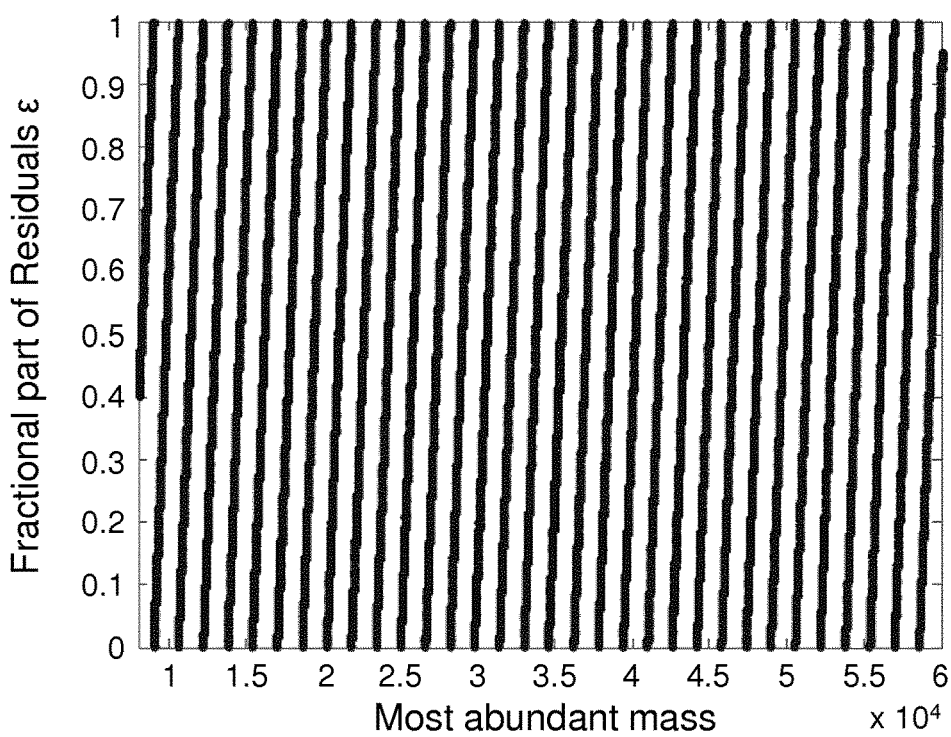
Figure 2E:
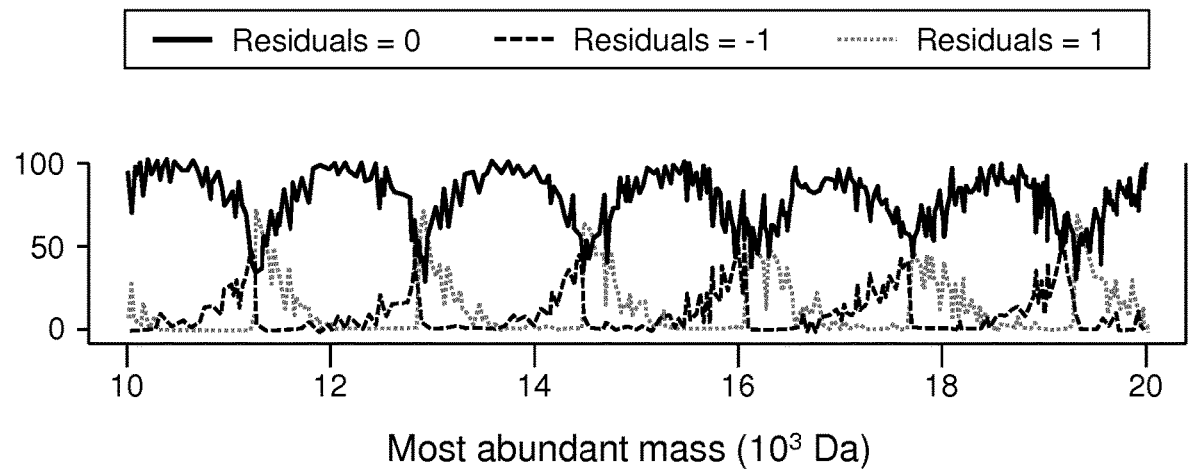

This is represented in FIG. 2D, where $\varepsilon_{frac}$ is plotted as a function of $M_{MostAb}$, neglecting the integer part ($\varepsilon_{int}$). The result is a sawtooth pattern which can be easily modelled. The vast majority of $\varepsilon_{int}$ values are at 0 or ±1 Da, with only 3.8% at ±2 Da, and the values ±3 or ±4 Da together occurring in less than 0.05% of cases. As such, for over 96% of all proteins, the model shown in FIG. 2D allows, for a given value of $M_{MostAb}$, to calculate three potential values for $M_{Mono}$, spaced 1 Da apart, one of which is very likely to match the theoretical value to within a few ppm. A final refinement of this model allows to choose between these three values and is shown in FIG. 2E, where the probability to the nearest integer value to the residuals is plotted as a function of $M_{MostAb}$, allowing to arrive at a single predicted $M_{Mono}$ value for a given $M_{MostAb}$.

Example 2—Determination of the Theoretically Most Abundant Mass—Dealing with Imperfect Data The workflow outlined in Example 1 applies to theoretical experimental data, which can be considered as 'perfect' experimental data. However, for the processing of real experimental data, data imperfections must be taken into account. For instance, at the typical precursor ion populations observed in top-down proteomics, it can be shown that the probability of the experimentally observed most abundant isotope peak not matching the theoretically predicted one, is sufficiently high that it should not be neglected. This probability is further increased by the introduction of a small amount of noise, which can also cause a minor distortion of the relative intensities of isotope peaks.

Fortunately, neither poor ion statistics, nor the presence of a limited degree of noise, induce a significant shift in measured m/z values for the individual isotope peaks, and thus their masses are still measured with an accuracy in the low-ppm range. As isotope peaks are by definition spaced 1 Da apart, erroneously selecting a peak adjacent to the theoretically most abundant one introduces an error of $10^6/M_{MostAb}$ ppm. Accordingly, in the precursor range between 10-100 kDa, typical for top- and middle-down proteomics, this would therefore introduce an error of 10-100 ppm. It is thus a much more significant source of error than the mass accuracy of the instrument, when the peak for which the highest intensity is observed, is automatically assumed to be the theoretically most abundant one. Thus, by introducing a solution to the poor accuracy associated with the observed average mass in a spectrum, a new problem is introduced on determining the theoretically most abundant mass even if this peak is not the most abundant one in an observed spectrum.

Three remedial measures can be proposed to aid in the selection of the theoretically most abundant peak.

1. By adjusting the instrument settings, ion statistics can be improved by enabling sum spectra or increasing the number of charges. However, caution should be applied to avoid overfilling the trap.
2. Multiple MS1 spectra of the same compound can be collected. These spectra can be used to pinpoint the most abundant mass as further described in Example 3.
3. If the previous two measures are not practical, then the most abundant peak can be selected from an averagine model [Senko et al; J Am Soc Mass Spectrom (1995) 6, 229-233, incorporated herein by reference]. This method implies that the theoretically most abundant peak is chosen from a scaled averagine molecule with the same average mass as that observed in the spectrum. This method is described in the next paragraph.

Due to natural or technical factors $M_{Average}$ can be shifted substantially, considerably more than expected from the specifications of high-end instruments. However, the (stochastic) effects that poor ion statistics and/or noise have on this value are typically far smaller than the error of 1 (or several) Da introduced by inadvertent selection of the wrong isotope peak as most abundant mass.

Furthermore, the average mass is consistently higher than the most abundant mass, and the difference between both values is almost never larger than 1.2 Da. This insight already reduces the number of candidate peaks to one or two.

For selecting between these candidate most abundant peak mass, an averagine model can be adopted, as represented in FIG. 3. FIG. 3 shows a plot of the values of $(M_{Average}-M_{MostAb})$ vs. $M_{Average}$ for human proteins in the UniProt database, showing this difference almost always has a value between 0 and 1, and revealing periodicity as a function of $M_{MostAb}$. The simple averagine model correlates the most abundant mass to the average mass ($M_{Average}$) and can again be modelled by a sawtooth pattern. If we compare the observed pattern to that generated by the averagine model, we see that the values for $(M_{Average}-M_{MostAb})$ rarely deviate from the model by more than about 0.2 Da. As the candidate peaks for $M_{MostAb}$ are by definition spaced 1 Da apart, this accuracy is sufficient to uniquely identify a single observed isotope peak as the theoretically most abundant one. However, the averagine model turns out to be most useful for masses up to around 20 kDa, after which the spread of the values for $(M_{Average}-M_{MostAb})$ becomes too large to allow reliable prediction of the approximate (to within <0.5 Da) most abundant mass. The fact that $(M_{Average}-M_{MostAb})<1.2$ Da can, however, still be used to drastically reduce the number of candidate peaks for spectra of proteins up to several hundred kDa in size.

Example 3—Proof-of-Concept: Mass Spectrometry of Equine Apo-Myoglobin

Spectra of equine apo-myoglobin (20 µg/mL in 49/50/1 H2O/acetonitrile/formic acid) were acquired on a Thermo LTQ Orbitrap Velos, operated at a resolution of 100,000 at 400 m/z and 1,000,000 charges were accumulated in the LTQ for analysis in the Orbitrap. Ionization here was typically performed through nano-ESI using a TriVersa NanoMate (Advion BioSciences, Ithaca, N.Y., USA). Calibration was performed using a standard calibration mix containing n-butylamine, caffeine, MRFA, and Ultramark 1621 (Pierce LTQ Velos ESI Positive Calibration Solution, Thermo catalog number 88323). In general, lyophilized myoglobin was dissolved in the appropriate buffer and used without further purification. For native analysis, 100 mM aqueous ammonium acetate (pH=6.8) was typically used, while 50:50 H2O:methanol or 50:50 H2O:acetonitrile were typically used to denature proteins, with 0.1% formic acid added in both cases. Conversely, for native analysis of the complexes, the lyophilized protein was typically dissolved at a concentration of 1 mg/mL in 100 mM aqueous ammonium acetate and desalted at least twice using Micro Bio-Spin P-6 gel columns (Bio-Rad, Hercules, Calif., USA).

Figure 4A:
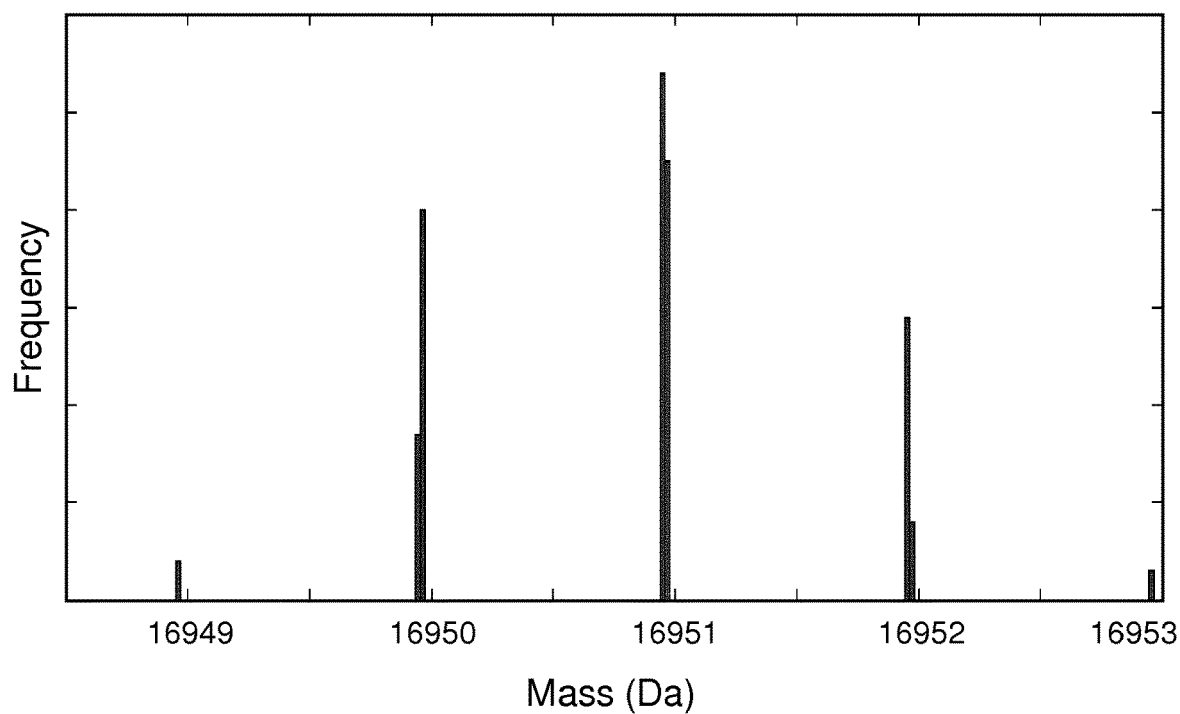

In order to evaluate the scan-to-scan stability of the monoisotopic mass predicted using the model and algorithm of Example 1, 200 spectra of intact apo-myoglobin (average mass 16951.26 Da) were acquired and independently processed. For each scan, the experimentally most abundant mass as well as the average mass were determined after isotopic peak picking and charge deconvolution. A histogram of the number of spectra in which each signal between 16949 and 16954 Da occurred as the base peak with most abundant mass is shown in FIG. 4A. It is clear from this figure that, although the signal at approximately 16950.9 (i.e. the theoretically most abundant mass) occurs as the experimentally most intense peak in a majority of the spectra, the experimentally most abundant peak is located 1 or 2 Da away from the theoretical value in nearly 50% of these spectra, even using a fairly high Automatic Gain Control (AGC) target of $10^6$ charges.

We can correct for this using the procedure outlined in Example 2. The measured average mass, while showing a systematic deviation of nearly 10 ppm from the calculated value, is relatively constant between scans, and only fluctuates in a range approximately 20 ppm (0.36 Da) wide. In contrast, due to poor ion statistics, this range is 240 ppm (4 Da) wide for the observed most abundant mass.

Figure 4B:
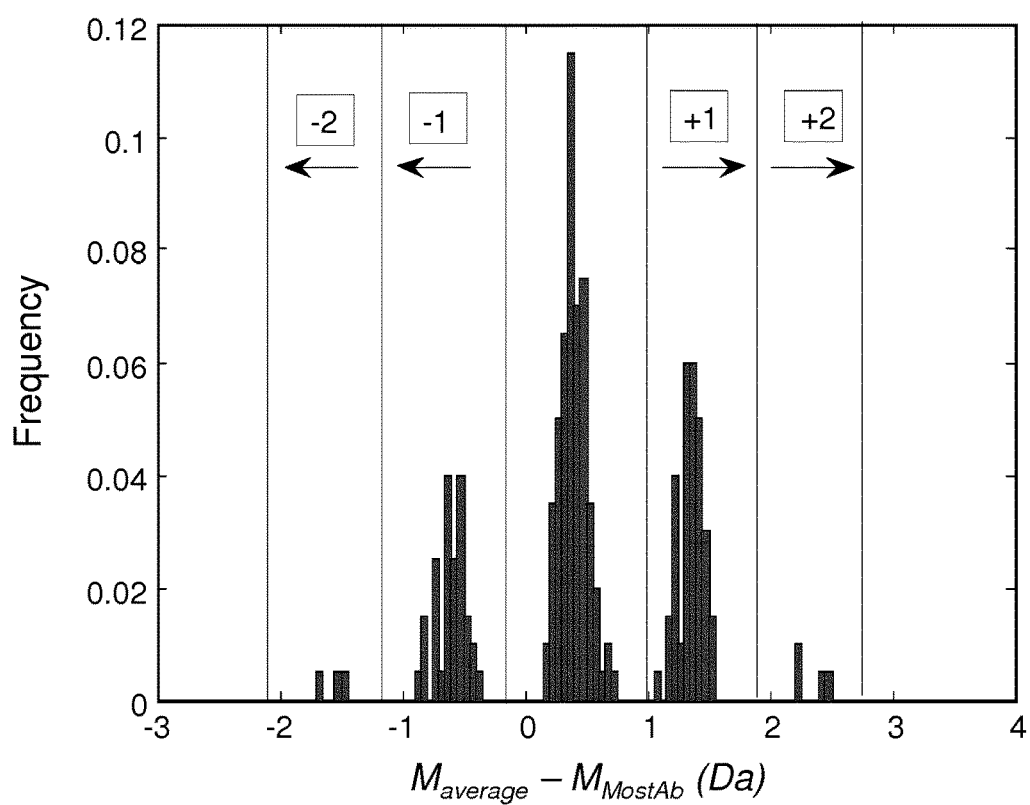
Figure 4C:
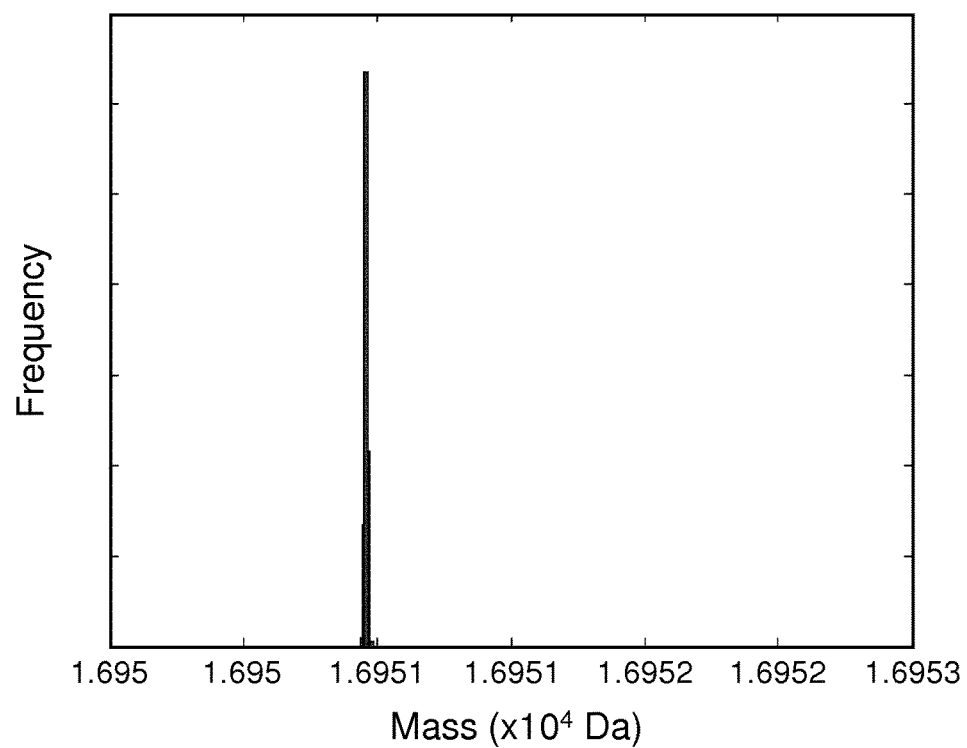
Figure 4D:
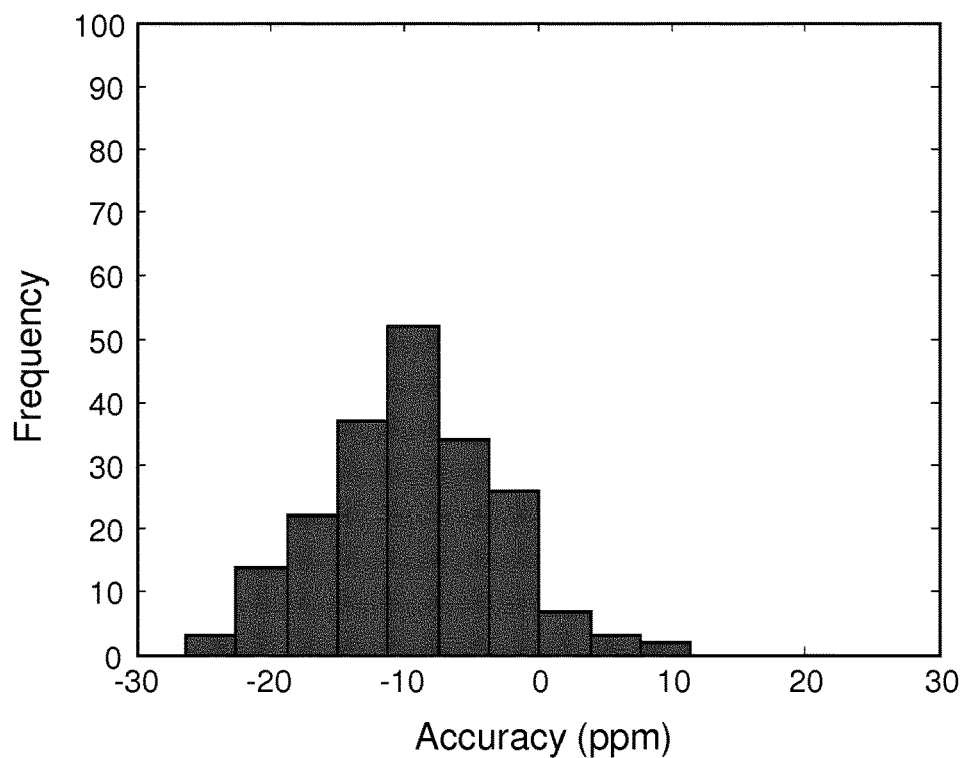
Figure 4E:
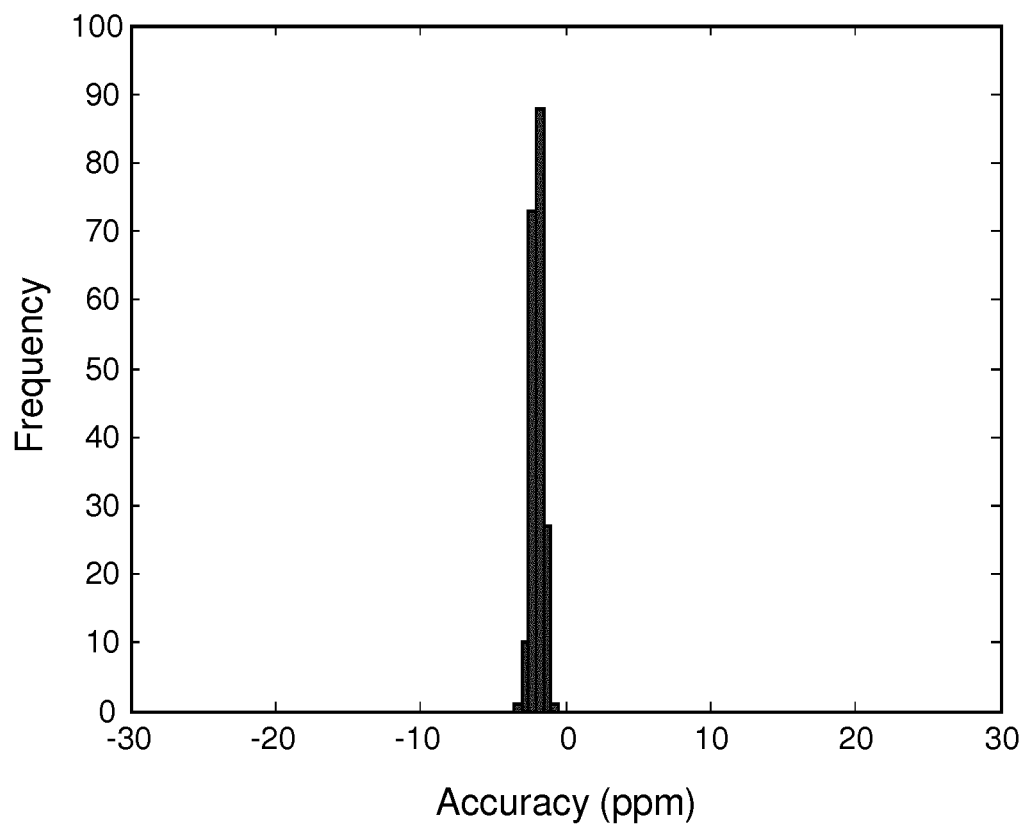

A histogram of the observed values of ($M_{Average} - M_{MostAb}$), as shown in FIG. 4B, shows clear clusters, corresponding to the clusters observed in FIG. 4A. In the correction procedure, we identify the cases in which the incorrect peak was selected and add or subtract 1 or 2 Da, as indicated in FIG. 4B. The result of this correction is shown in FIG. 4C, where essentially the same value for $M_{MostAb}$ is generated from all 200 spectra. Finally, FIGS. 4D and 4E show the deviation of the calculated average mass (as a weighted sum of the observed masses and intensities of the isotope peaks) and monoisotopic mass (predicted using the methods of the present invention) from the theoretical values for the 200 spectra. As mentioned, this ranges between +1.11 and −20.37 ppm (interval width 21.48 ppm; average −9.63 ppm) for the average mass.

However, after correction, the predicted monoisotopic mass only shows a deviation from the calculated value between −1.16 and −2.54 ppm (interval width 1.38 ppm; average −1.85 ppm). This difference is in accordance with the accuracy and precision expected from the instrument specifications.

Example 4

The workflow presented in FIG. 5 is further illustrated below. The highest peak in the spectrum, representing the (experimental) most abundant mass has a value of 2119.88 m/z. Next, the masses of the three peaks to the left and three peaks to the right of the most abundant peak are selected and stored in a temporary vector: temp=[2119.50, 2119.63, 2119.75, 2119.88, 2120.00, 2120.13, 2120.25]. Next, a temporary vector called diffTemp is calculated that contain the differences between the $(i+1)^{th}$ and $i^{th}$ element in de vector temp. Inverse every value in the vector and round these values, which results in ([7.6923, 8.3333, 7.6923, 8.3333, 7.6923, 8.3333]). Next, the charge state is determined by majority vote on the obtained result and the most abundant m/z value is charge deconvoluted with the obtained charge z and the mass of a proton equal to 1.007276466879 Da. Doing so, the most abundant mass becomes 16950.982 Da. The monoisotopic mass can then be calculated based on the first linear model, as determined in example 1, i.e 16940.9587041111 Da. In combination with the piecewise linear model (sawtooth model) that is valid for the range between 16154.2346636253 and 17754.6184585493 Da, (i.e., −10.6081613553838+0.000625700928464534× mass=−0.00191617959819723 Da), the predicted monoisotopic mass now becomes 16940.96 Da. Finally, based on the probability of $\varepsilon_{int}$ being −1, 0, or 1 as a function of the most abundant mass $M_{MostAb}$, the probability of $\varepsilon_{int}$ being 0 for the most abundant mass of 16950.982 was significantly higher than the probability of $\varepsilon_{int}$ being −1 or 1. Accordingly, the final monoisotopic mass value equals 16940.96+ 0=16940.96.

The invention claimed is:

1. A method for determining the monoisotopic mass $M_{Mono}$ of a macromolecule having a mass of at least $10^5$ Da from a mass $M_{mono}$ spectrometry spectrum of said macromolecule, the spectrum comprising a set or plurality of isotopic peaks representing an isotope distribution of said macromolecule, comprising the steps of:
  (a) deriving the most abundant mass $M_{MostAb}$ from the set or plurality of isotopic peaks; and
  (b) determining the monoisotopic mass $M_{Mono}$ from the most abundant mass $M_{MostAb}$, using the following model $$M_{Mono}=\alpha+\beta M_{MostAb}+\varepsilon;$$

wherein $\alpha+\varepsilon$ is an intersect and $\beta$ is a scalar slope obtainable by fitting the slope of the plot of the monoisotopic mass in function of the most abundant mass for a plurality of macromolecules from a macromolecule database; and $\varepsilon$ is a scalar residue of the form $\varepsilon=\varepsilon_{int}+\varepsilon_{frac}$, $\varepsilon_{int}$ being an integer selected from the group consisting of −2, −1, 0, 1, and 2, and $\varepsilon_{frac}$ being a sawtooth function of $M_{MostAb}$, wherein $\varepsilon_{frac}=\varepsilon-$round ($\varepsilon$), with round($\varepsilon$) being the round function of $\varepsilon$.

2. The method according to claim 1 wherein the macromolecule is a protein.

3. The method according to claim 1 wherein the domain of $\varepsilon_{frac}$ is [0,1].

4. The method according to claim 1 wherein selecting $\varepsilon_{int}$ comprises the steps: modelling or quantifying the probability of $\varepsilon_{int}$ being −1, 0, or 1 as a function of the most abundant mass $M_{MostAb}$; and selecting −1, 0, or 1 as the value of $\varepsilon_{int}$ when the probability that $\varepsilon_{int}$ respectively equals −1, 0, or 1 is the highest.

5. The method according to claim 1 wherein $\beta$ ranges between 0.99 and 1.

6. The method according to claim 1, wherein step (a) comprises the steps of:
  (a1): calculation of the average mass $M_{Average}$ (exp) of the plurality of isotopic peaks within the mass spectrum of the macromolecule and selection of the experimental most abundant mass $M_{MostAb}$ (exp) as the isotopic peak with the highest intensity in the plurality of isotopic peaks within the mass spectrum;
  (a2): calculation of [$M_{Average}$ (exp)−$M_{MostAb}$ (exp)] in order to determine if $M_{MostAb}$ (exp) corresponds to the theoretical $M_{MostAb}$;

(a3): if $0.1 \leq [M_{Average}(exp) - M_{MostAb}(exp)] \leq 1.1$, then $M_{MostAb}(exp)$ is selected as the correct $M_{MostAb}$, corresponding to the theoretical most abundant mass;

if not $0.1 \leq [M_{Average}(exp) - M_{MostAb}(exp)] \leq 1.1$; then the correct $M_{MostAb}(exp, cor)$ is selected as the mass corresponding to the mass of the peak positioned one or two peaks before or after the $M_{MostAb}(exp)$ isotopic peak so that $0.1 \leq [M_{Average}(exp) - \{M_{MostAb}(exp, cor)\}] \leq 1.1$, wherein $M_{MostAb}(exp,cor)$ is selected as the correct $M_{MostAb}$, corresponding to the theoretical most abundant mass.

7. The method according to claim 2 wherein in step (a), the most abundant mass $M_{MostAb}$ is approximated by the most abundant mass of a scaled averagine model, the scaled averagine model having an average mass equal to the average mass of the isotopic mass spectrum of the protein.

8. The method according to claim 1 further comprising the step c of identification of the macromolecule using $M_{Mono}$ of step (b).

9. A computer program product comprising computer-readable instructions which, when executed on a computer, cause the method to execute a method according to claim 1.

10. The method of claim 1 wherein $\varepsilon_{int}$ is an integer selected from the group consisting of −1, 0, and 1.

11. The method of claim 1 wherein the macromolecule has a mass of at least $10^6$ Da.

12. The method of claim 1 wherein the macromolecule has a mass of at least $10^7$ Da.

* * * * *